United States Patent [19]

Sherwood et al.

[11] 4,335,073
[45] Jun. 15, 1982

[54] NOX CONVERSION EFFICIENCY DETECTOR

[75] Inventors: Loran D. Sherwood, Walled Lake, Mich.; Jack J. Keegan, La Habra; Stephen A. Gniewek, Glendora, both of Calif.

[73] Assignee: Beckman Instruments, Inc., Fullerton, Calif.

[21] Appl. No.: 260,238

[22] Filed: May 4, 1981

[51] Int. Cl.³ ............................................. G01N 21/76
[52] U.S. Cl. ......................................... 422/83; 73/23; 422/52
[58] Field of Search ................... 422/52, 95, 86, 83; 23/232 R; 73/23

[56] References Cited

U.S. PATENT DOCUMENTS

| | | | |
|---|---|---|---|
| 3,070,988 | 1/1963 | Kapff et al. | 73/1 |
| 3,247,702 | 4/1966 | Houser et al. | 73/1 |
| 3,407,646 | 10/1968 | Traver | 73/23 |
| 3,495,437 | 2/1970 | Estes et al. | 73/1 |
| 3,973,914 | 8/1976 | Van Heusden | 422/52 |
| 4,018,562 | 4/1977 | Parks et al. | 422/52 X |
| 4,101,282 | 7/1978 | Ririe | 73/23 |
| 4,106,910 | 8/1978 | Saunders | 23/232 R |
| 4,114,419 | 9/1978 | Kimbell | |
| 4,257,777 | 3/1981 | Dymond et al. | 422/52 X |

FOREIGN PATENT DOCUMENTS 811973  5/1969  Canada.

OTHER PUBLICATIONS

Instruction Manual, Model 100, NOx Generator, Thermo Electron Corp., 45 First Ave., Waltham, Mass. 02154

Primary Examiner—Ronald E. Serwin
Attorney, Agent, or Firm—Robert J. Steinmeyer; Paul R. Harder; Edward C. Jason

[57] ABSTRACT

An improved apparatus for facilitating the practice of a method for determining the conversion efficiency of the NOx converter of an oxides of nitrogen analyzer. An improved ozone control assembly facilitates the control of the ozone content of the gas mixture that is applied to the input of the analyzer. An improved gas flow regulating arrangement allows the composition of the gas mixture to be changed without affecting the flow rate thereof. Together, these structures improve the stability and ease of use of the conversion efficiency detector.

23 Claims, 2 Drawing Figures

NOX CONVERSION EFFICIENCY DETECTOR

BACKGROUND OF THE INVENTION

In gas analyzers which measure the oxides of nitrogen content of a sample gas stream, it is the practice to perform the measurement in two stages. In the first stage, the sample gas stream is mixed with an ozone containing gas stream and the photons emitted as a result of the reaction therebetween are measured with a photomultiplier tube to obtain a first oxides of nitrogen reading. In the second stage, the higher oxides of nitrogen in the sample gas stream, known collectively as NOx, are reduced to nitric oxide by the action of a catalytic converter that is commonly referred to as an NOx converter. After reduction, the gas stream is again mixed with an ozone containing gas stream, the resulting photons being measured with a photomultiplier tube to obtain a second oxides of nitrogen reading. The first reading is then taken as the NO content of the sample stream, and the difference between the second and first readings is taken as the NOx content of the sample stream.

Because the efficiency of the NOx converter in reducing higher oxides of nitrogen to nitric oxide is crucial to the accuracy of analyzers of the abovedescribed type, it has become the practice to include measurements of the efficiency of the NOx converter as a regular part of the procedure for using oxides of nitrogen analyzers. The method by which the efficiency of the NOx converter is measured involves applying to the sample inlet of the analyzer a series of gases the compositions and flow rates of which are related to the operating conditions of the analyzer. At various points in the measurement process analyzer output readings are recorded for later substitution into an equation, the solution of which yields the desired NOx conversion efficiency.

Both the above conversion efficiency equation and the readings to be recorded for substitution therein are well known to those skilled in the art. Moreover, the conversion efficiency equation, the readings used therein, and the procedures and conditions under which the readings are taken form the subject matter of regulations which have been promulgated by the Environmental Protection Agency for purposes of standardization. The latter regulations are set forth in Title 40 of the Code of Federal Regulations, Section 86.132-84, entitled "Oxides of Nitrogen Analyzer Calibration". The text of these regulations is hereby expressly incorporated herein by reference.

In order to facilitate the practice of the subject method, there have been developed special devices, known as NOx converter efficiency detectors, that are designed to aid in establishing and adjusting the gas flows used during the measurement process. In a typical one of such detectors, there was provided an inlet for oxygen or other oxygen containing gas, a second inlet for supplying a gas of known nitric oxide content, and an outlet for connection to the sample inlet of an oxides of nitrogen analyzer. Also included in such converter efficiency detectors was an ozone generator for converting a portion of the oxygen in the oxygen containing gas into ozone. The desired ozone concentration was then established by varying the operating voltage applied to the ozone generator. Finally, the efficiency detectors included various valves and pressure regulators by means of which the flow of gases could be initiated and adjusted.

While NOx converter efficiency detectors of the above-described type greatly facilitated the efficiency measurement process, they had several shortcomings which limited their utility. One shortcoming was the relative difficulty of making the final, fine adjustments of the ozone level in the oxygen containing gas stream. Small changes in the excitation of the ozone generator could, for example, cause relatively large changes in ozone concentration. This, in turn, led to an iterative adjustment process that greatly increased the amount of time necessary to complete the overall efficiency measurement.

A second shortcoming of converter efficiency detectors of the above-described type is that they are subject to unanticipated fluctuations in the flow rates of the gases that are applied to the inlet of the oxides of nitrogen analyzer. If, for example, the quantity of the oxygen containing gas that was added to the nitric oxide containing gas was changed, changes would occur in the rate of flow of the mixture of these gases at the input of the analyzer. As a result, the accuracy of the efficiency computation, which is based on an assumed constant overall gas flow rate, was adversely affected. Thus, the interdependence of the gas flow rates within the detector tended to reduce the overall accuracy of converter efficiency measurements.

SUMMARY OF THE INVENTION

In accordance with the present invention, there is provided an improved converter efficiency detector which is free of the above-described shortcomings. One respect in which the efficiency detector of the invention has been improved is the inclusion therein of an ozone control assembly that allows the ozone concentration to be finely adjusted without varying the operating voltage or current of the ozone generator. More particularly, the detector of the invention is provided with an improved mechanical ozone control arrangement that allows ozone concentration adjustments that are both rapid and accurate. As a result, the detector of the invention may be adjusted more conveniently and confidently than previously known detectors.

Another respect in which the converter efficiency detector of the invention is improved over previously known detectors is the inclusion therein of a highly advantageous flow regulating arrangement. This flow regulating arrangement maintains the gas flow rate at the input to the oxides of nitrogen analyzer at a constant value, in spite of changes in the rate of flow of the oxygen containing gas stream before, during or after the addition of ozone. As a result, the converter detector of the invention establishes highly stable gas flow conditions and thereby assures efficiency measurements of improved accuracy and reliability.

Also contemplated by the present invention is improved control circuitry which facilitates the establishment of the successive gas flow conditions that must exist during the taking of readings for use in the efficiency formula.

DESCRIPTION OF THE PREFERRED EMBODIMENT

Figure 1:
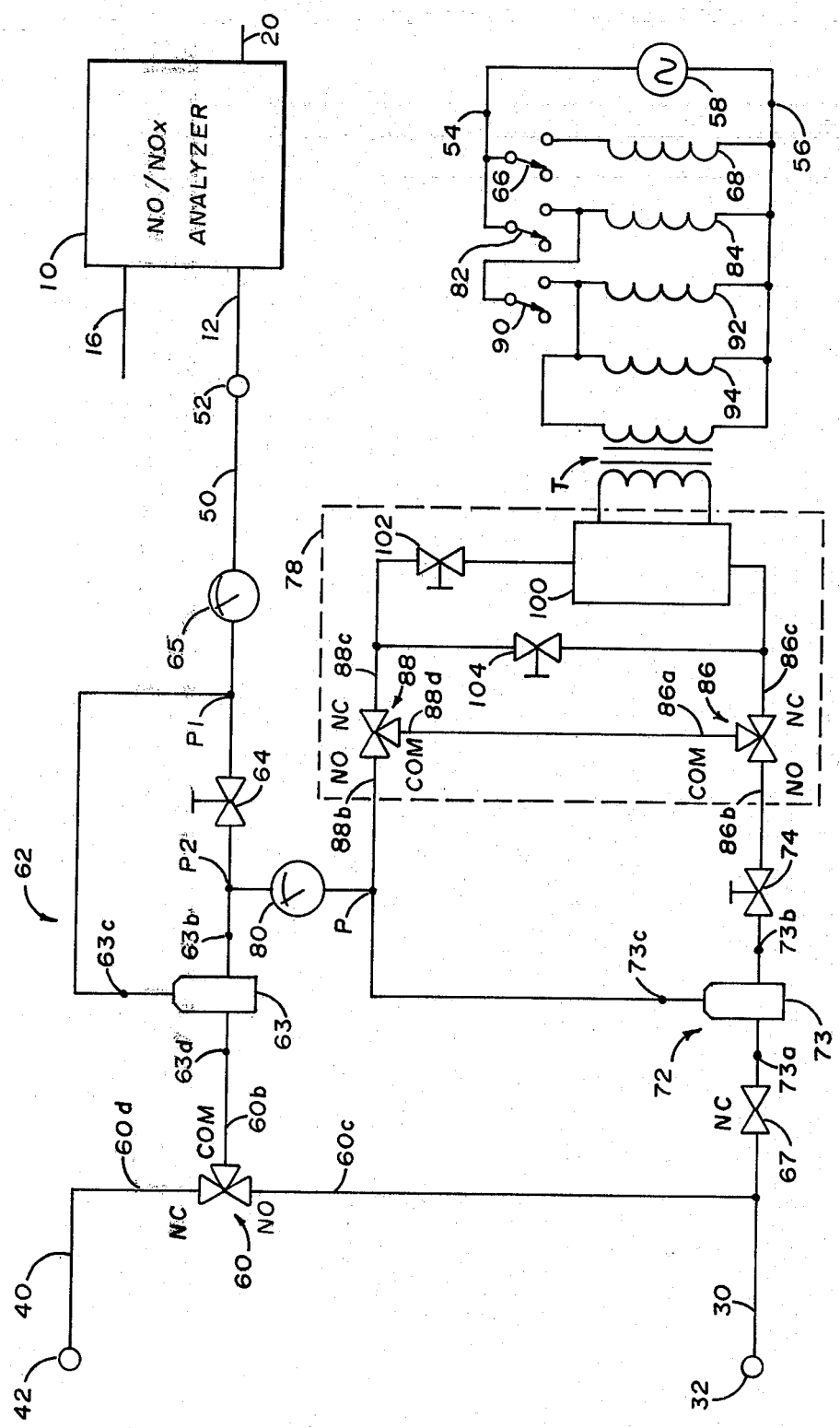
FIG. 1 is a block diagram of an NOx converter efficiency detector that has been constructed in accordance with the present invention.

Referring to FIG. 1, there is shown an oxides of nitrogen analyzer 10 having a simple inlet line 12 for connection to a source of sample gas and an oxygen inlet line 16 for connection to a source of air or other oxygen containing gas. Analyzer 10 also includes an exhaust or outlet line 20 through which the gases used in the measurement process may be exhausted for safe disposal. Analyzer 10 may, for example, comprise a chemiluminescent analyzer of the type sold by the assignee of the present invention under Model No. 951A. Generally speaking, analyzer 10 is an instrument of the type that performs its measurements in two stages or steps. In a first step, commonly referred to as operation in the NO mode, the nitric oxide content of the sample gas is measured by reacting the sample gas with an ozone containing gas and measuring the resulting photons with a photomultiplier tube. In a second step, commonly referred to as operation in the NOx mode, the sample gas is directed through a catalytic converter which reduces the higher oxides of nitrogen contained therein (mostly nitrogen dioxide or $NO_2$) to nitric oxide. The resulting gas is then reacted with an ozone containing gas and measured as before. The reading obtained in the first step is then taken as the quantity of nitric oxide present, and the difference between the first and second readings is taken as the quantity of higher oxides of nitrogen present. Naturally, with instruments of this type, the effectiveness or efficiency of the converter in reducing higher oxides of nitrogen to nitric oxide is of vital importance to the overall accuracy of the readings obtained.

The remainder of FIG. 1 depicts the preferred embodiment of the NOx converter efficiency detector of the present invention. This detector includes a first inlet duct or line 40 for connection to a source of nitric oxide of known concentration. This source (not shown) may, for example, comprise a tank of a standard or span gas such as a mixture of nitric oxide and nitrogen. Inlet 40 is ordinarily connected to the source of standard gas through a suitable inlet coupling 42, and through the pressure regulator-indicator devices that are normally mounted on the tank.

The detector of FIG. 1 also includes a second inlet duct or line 30 for connection to a source of an oxygen containing gas. This gas source (also not shown) may, for example, comprise a tank of a "zero" gas such as oxygen or compressed air, although other oxygen containing gas may also be used. Inlet 30 is ordinarily connected to the source of zero gas through a suitable inlet coupling 32 and through the pressure regulator-indicator devices that are normally mounted on the tank.

The detector of FIG. 1 is also provided with an outlet duct or line 50 for connection to the sample inlet line 12 of analyzer 10, through a suitable outlet coupling 52. This outlet line, which forms a part of the main gas flow path through the detector, supplies analyzer 10 either with zero gas from inlet line 30, or with standard gas from inlet line 40, or with an ozone containing mixture thereof. The purposes of these different gases will be described more fully presently. Finally, the detector of FIG. 1 includes power inlet leads 54 and 56 for connection to a suitable a.c. power source 58.

In instances in which NOx efficiency determinations must be done with great frequency, detector outlet 50 may be connected to sample inlet 12 through one passage of a three-way source-select valve, the other passage therethrough being connected to a source of sample gas. This structure then affords the ability to switch the detector in or out with a solenoid, as needed, without having to manually connect and disconnect coupling 52.

Generally speaking, the purpose of the converter efficiency detector may be understood from the following simplified summary of the sequence of its operating conditions. Firstly, the detector supplies analyzer 10 with a gas stream having a known NO content. In this condition the output reading of analyzer 10 is calibrated in preparation for later measurements. Secondly, the detector supplies analyzer 10 with a gas stream in which some of the NO is converted to NOx as a result of the addition of an ozone containing gas. The ozone concentration is selected to produce a predetermined decrease in the output reading of analyzer 10. Thirdly, analyzer 10 is switched from its NO mode to its NOx mode in an attempt to convert to NO the NOx that resulted from the addition of ozone. If the converter in analyzer 10 is 100% efficient, all of the NOx that resulted from the addition of ozone will be re-converted to NO, causing the analyzer output reading to return to its pre-ozone value. Conversely, the failure of the analyzer output reading to return to its pre-ozone value is an indication of the amount by which the analyzer's NOx converter is less than 100% efficient. Thus, the converter efficiency detector of the invention operates with an NOx analyzer and facilitates the application thereto of a sequence of gases.

As will be explained more fully later, the complete measurement process is somewhat more complicated because it includes additional steps that allow the use of standard and zero gases that contain significant quantities of higher oxides of nitrogen. These steps have been omitted from the foregoing simplified description, however, since they tend to obscure the broader aspects of the overall process.

The gases that are applied to analyzer 10 through output line 50 are derived from the standard gas entering detector inlet 40, the zero gas entering detector inlet 30, or from a mixture of the two. These gases flow to outlet 50 through one of three paths through the detector. The first of these flow paths includes standard gas inlet line 40, the normally closed passage between lines 60a and 60b of a three-way solenoid valve 60, a first adjustable flow regulating assembly 62 (to be described more fully presently) and a flow indicating gauge or flowmeter 65. This flow path is active when nitric oxide containing gas is being supplied to analyzer 10, and is established when a switch 66 is operated from the position shown in FIG. 1, that is, when the coil 68 that controls solenoid valve 60 is energized.

The second flow path through the detector includes zero gas inlet line 30, the normally open passage between lines 60b and 60c of solenoid valve 60, flow regulating assembly 62 and flowmeter 65 to outlet line 50. This flow path is active only when pure zero gas is being supplied to analyzer 10, and is established when switch 66 is in the position shown in FIG. 1, that is, when coil 68 is de-energized. Thus, three-way valve 60 serves as a source-select valve for selectably connecting regulating assembly 62 to the source of standard gas or to the source of zero gas.

The third flow path for gas through the detector includes zero gas inlet line 30, a normally closed solenoid valve 67, a second adjustable flow regulating assembly 72 (to be described more fully presently), an ozone control assembly 78, a flow indicating gauge 80, a part of first flow regulating assembly 62, and flowmeter 65 to outlet line 50. The third gas flow path is active when analyzer 10 is to be supplied with a mixture of standard gas from inlet 40 and ozonized or unozonized zero gas from inlet 30. The third gas flow path is established when a switch 82 is operated from the position shown in FIG. 1, that is, when the coil 84 that controls the state of solenoid valve 67 is energized.

The above-described third flow path is further divided, within ozone control assembly 78, into a bypass or non-ozonating flow path through which zero gas may flow without any of the oxygen therein being converted to ozone, and a non-bypass or ozonating flow path through which the zero gas may flow with some of the oxygen therein being converted to ozone. The bypass flow path includes the normally open passage between lines 86a and 86b of an upstream bypass solenoid valve 86 and the normally open passage between lines 88a and 88b of a downstream bypass solenoid valve 88. The bypass path through ozone control assembly 78 is established when a switch 90 is in the position shown in FIG. 1, that is, when the coils 92 and 94 that control valves 86 and 88, respectively, are deenergized.

The ozonating path through ozone control assembly 78 includes the normally closed passage between lines 86b and 86c of solenoid valve 86 and the normally closed passage between lines 88b and 88c of solenoid valve 88. The latter path also includes an ozone generator 100 which may be of any suitable type. As will be described more fully later, ozone generator 100 is connected to the bypass solenoids through a series flow control device 102, and a parallel flow adjusting device 104. In accordance with one feature of the present invention, these devices allow the ozone content to be finely adjusted, over a wide range of values, without the necessity of changing the operating voltage or current of ozone generator 100.

In view of the foregoing, it will be seen that ozone control assembly 78 directs the flow of gas in the third gas flow path through either a bypass flow path in which no ozone is introduced into the oxygen containing gas entering through inlet 30, or an ozonating flow path in which a controllable quantity of ozone is introduced into the oxygen containing gas entering through inlet 30.

The terms first, second and third gas flow paths have been adopted for use herein, as a convenience, to avoid having to refer to a plurality of individual elements when making reference to a gas flow path as a whole. It should not be inferred from these terms, however, that the three gas flow paths are mutually exclusive. There are, for example, conditions in which gas will flow through the first and third flow paths at the same time, for mixing purposes. In addition, it will be understood that the gas flow paths through the detector may, for certain purposes, be more conveniently referred to by terms other than first, second or third. For example, all of the gases or gas mixtures that are supplied directly to analyzer 10 flow through flow regulating assembly 62 and outlet line 50. As a result, gas flowing through assembly 62 may be said to be flowing through the "main" gas flow path through the detector. On the other hand, gas flowing through flow regulating assembly 72 is applied to analyzer 10 only indirectly, i.e., after being passed through and processed by regulating assembly 62. As a result, gas flowing through assembly 72 may be said to be flowing through the "secondary" gas flow path through the detector. As will be explained more fully later, the present invention contemplates the simultaneous and cooperative regulation of gas flow in the main and secondary gas flow paths.

Ozone generator 100 may be of the type which produces ozone by the chemical conversion of the oxygen that is present in a gas stream that flows therethrough. This conversion preferably occurs by exposing the oxygen to ultraviolet light from an ultraviolet lamp. It is, however, possible to use corona discharge type ozone generators, among others, for practicing the present invention. In the embodiment of FIG. 1, ozone generator 100 is energized from a.c. source 58 through a suitable transformer T. Because ozone generators that employ ultraviolet lamps are well known to those skilled in the art, the structure and operation of generator 100 will not be further described herein.

In accordance with an important feature of the present invention, the ozone content of the gas in the third gas flow path is adjusted, not by varying the operating voltage or current of the ozone generator, but rather by adjusting the settings of series and parallel connected flow control devices 102 and 104 which may take the form of needle valves. One advantage of controlling the ozone content by the mechanical means contemplated by the present invention is that such means allow the ozone content of the gas in the third flow path to be varied over a wide range of values and yet be finely adjusted about each value in that wide range.

The ozone control activity of ozone control assembly 78 will now be described. In the preferred embodiment, flow control devices 102 and 104 are manually adjustable valves that are substantially similar, in size and characteristics, both to one another and to valve 74. During the initial set-up of the detector, valve 74 is adjusted to provide the desired flow rate in the third gas flow path. Under this condition, bypass solenoids 86 and 88 are in their bypass condition and valves 102 and 104 are in their fully open state. Because valve 74 is only partially open, while valves 102 and 104 are fully open, the latter valves have a flow resistance that is negligible in comparison with that of valve 74. As a result, the shift in gas flow which results from the establishment of the normally closed path through solenoid valves 86 and 88 produces no significant change in the rate of flow of gas through the third gas flow path. Ozone is, however, introduced into the third gas flow path as a result of this shift, the quantity of ozone being dependent upon the level of excitation of ozone generator 100 and the $O_2$ content of the zero gas, among other factors. For the sake of convenience, the quantity of ozone that is present in the third gas flow path when valves 102 and 104 are both fully open will hereinafter be referred to as the nominal quantity or nominal concentration of ozone.

If the nominal quantity of ozone is greater than that necessary for conversion efficiency determinations, the ozone level may be reduced by partially closing valve 102. This causes more of the gas in the third gas flow path to flow through valve 104 than flows through ozone generator 100 and valve 102. This diversion in gas flow, in turn, causes less of the gas in the third gas flow path to be exposed to the ozonating influence of ozone generator 100 than was the case when valves 102 and 104 were both in their fully open condition. As a result, the ozone level in the third gas flow path is reduced by an amount dependent upon the relative flow resistances of valves 102 and 104. Because valve 104 remains fully open, however, the combined effective flow resistance of valves 102 and 104 remains very much less than the flow resistance of valve 74. As a result, the ozone level reduction produced by valve 102 occurs without substantial effect upon the rate of gas flow through the third gas flow path, as previously fixed by valve 74 in conjunction with flowmeter 80.

If, on the other hand, the nominal quantity of ozone is less than that necessary for conversion efficiency determinations, the ozone level may be increased by leaving valve 102 in its fully open condition and by partially closing valve 104. This causes more of the gas in the third gas flow path to flow through valve 102 and ozone generator 100 than flows through valve 104. The latter condition, in turn, causes a greater proportion of the gas in the third gas flow path to be subjected to the ozonating influence of ozone generator 100 than was the case when valves 102 and 104 were both fully open. As a result, the ozone level in the third gas flow path is increased by an amount dependent upon the relative flow resistances of valves 102 and 104. Because valve 102 remains fully open, however, the combined effective flow resistance of valves 102 and 104 remains very much less than the flow resistance of valve 74. As a result, the ozone level increase produced by valve 104 occurs without substantial effect on the rate of flow of gas through the third gas flow path, as previously fixed by valve 74 in conjunction with flowmeter 80.

One particularly significant advantage of using series-parallel connected flow control devices 102 and 104 is that this configuration allows fine control over the ozone concentration of gas in the third gas flow path over a wide range of ozone concentration values. Assuming, for example, that parallel valve 104 is fully open and valve 102 is being adjusted, a 50% increase in the flow resistance of valve 102 will cause the percentage of gas that flows through valve 102 to drop from 50% to 30% of the gas flowing in the third gas flow path. Similarly, assuming that series valve 102 is fully open and that parallel valve 104 is being adjusted, a 50% increase in the flow resistance of valve 104 will cause the percentage of gas that flows through valve 102 and ozone generator 100 to increase from 50% to 66% of the gas flowing in the third gas flow path. Accordingly, since relatively large adjustments of valve 102 and 104 produce relatively small changes in the ozone concentration, it will be seen that the ozone level may be changed by small amounts, i.e., be finely adjusted, without having to make correspondingly small or critical mechanical adjustments of flow control devices 102 and 104.

In view of the foregoing, it will be seen that a detector constructed in accordance with the preferred embodiment of the invention allows the establishment of ozone concentrations which are either substantially in excess of or substantially less than the nominal concentration, and that any such concentration may be finely adjusted without the making of tiny or critical mechanical adjustments in flow control devices 102 and 104. In addition, it will be seen that so long as the flow resistance of valve 74 is substantially greater than the combined effective flow resistance of valves 102 and 104, the above-described adjustments may be made without significant effect on the rate of gas flow in the third flow path.

In certain applications, it may be found that the nominal ozone concentration is so high that all of the ozone concentration values necessary for proper detector operation may be provided by adjusting series flow control valve 102, without the need for adjustments in parallel flow control valve 104. If this is the case, parallel valve 104 may be replaced with a fixed flow restrictor having a flow resistance equal to that established by valve 104 in its fully open condition. Similarly, in certain applications, it may be that the nominal ozone concentration is so low that all of the ozone concentration values necessary for proper detector operation can be produced by adjusting parallel valve 104 without the need for adjustments to series valve 102. In such applications, series valve 102 may be replaced by fixed flow restrictor having a flow resistance substantially equal to that established by valve 102 in its fully open condition. Naturally since either of the above modifications limits the flexibility of the detector of the invention, these modifications should not be made unless it is certain that there will be no operating condition under which an ozone concentration that is beyond the range of the detector will be necessary.

While the preferred embodiment of the invention contemplates a substantially fixed flow resistance in one or the other of series and parallel valves 102 and 104, it is possible to practice the present invention in a way in which all of valves 74, 102 and 104 are between their fully open and fully closed conditions at the same time. Valve 74, for example, may be adjusted so that the flow rate of gas in the third gas flow path approximates the desired flow rate therethrough. Valves 102 and 104 may thereafter both be adjusted to bring the ozone concentration to approximately the desired value. Because, with such an approach, changes in each valve interact with and affect the rate of flow through each other valve, however, it may be necessary to repeat the just-describe adjustment sequence on an iterative basis until both the desired flow rate and the desired ozone concentration are achieved. As a result, such an approach is less convenient than the approach contemplated by the preferred embodiment. Because, however, even the less preferred approach provides both a wide range of ozone concentration values and the fine control of ozone concentration with respect to each valve in that range, even the less preferred embodiment represents a significant improvement over previously available efficiency detectors. Accordingly, it will be understood that all of the above-described embodiments are within the contemplation of the present invention.

As is well known, the rate of flow of gas through a given path is dependent both upon the driving pressure that is applied to the path and upon the flow resistance of the path. As a result, the flow rate of the gas that is supplied to analyzer 10 through outlet line 50 will be seen to be dependent both upon variations in the pressures of the gases supplied to inlet lines 30 and 40 and upon the settings of valves 102 and 104, among others. The effect of driving pressure variations is ordinarily taken into account by providing pressure regulators between the standard and zero gas sources and inlet lines 30 and 40. Prior to the present invention, however, the effects of changes in flow resistance that resulted from the adjustment of valves during a measurement sequence have not been taken into account. In accordance with another feature of the present invention, the effect of these flow resistance changes is substantially eliminated by providing a first adjustable flow regulating assembly 62 in the main gas flow path, by providing a second adjustable flow regulating assembly 72 in the secondary gas flow path, and by connecting the two flow regulating assemblies to one another in a manner that assures a constant rate of flow for the gas supplied to analyzer 10 through outlet line 50.

In the present embodiment, second adjustable flow regulating assembly 72 includes a differential type flow controller 73 having an inlet 73a, an outlet 73b, a control line 73c, a flow rate adjustment valve 74, and the connecting lines therebetween. Flow controller 73 may be of any of a number of commercially available types, but is preferably of the type in which the pressure at control line 73c controls the position of a plunger that is located in the gas flow path between inlet 73a and outlet 73b. The rate of flow at which controller 73 regulates flow therethrough may be changed by adjusting valve 74 while observing the resulting reading on flowmeter 80. Because flow control line 73c is directly connected to a point P that is just upstream of flowmeter 80, the rate of flow through the secondary gas flow path is unaffected by changes in the pressure drop across valve 74, or by changes resulting from the opening and closing of bypass solenoids 86 and 88, or from adjustments in the settings of valves 102 and 104 of ozone control assembly 78. Thus, flow regulating assembly 72 establishes a stable, adjustable rate of flow for gas in the secondary gas flow path through the detector.

Similarly, first flow regulating assembly 62 includes a differential flow controller 63 having an inlet 63a, an outlet 63b, a control line 63c, a flow rate adjustment valve 64 and the connecting lines therebetween. The rate of flow of gas through flow regulating assembly 62 may be changed by adjusting valve 64 while observing the resulting reading on flowmeter 65. Because control line 63c of controller 63 is connected directly to a point P1 that is just upstream of flowmeter 65, the rate of flow of gas through assembly 12 is unaffected by changes in the pressure across valve 64 or other flow variables that produce their effect upstream of point P1. Thus, regulating assembly 62 establishes a stable, adjustable rate of flow for gas in the main gas flow path through the detector.

In accordance with another important feature of the present invention, the rate of flow of gas through flow regulating assemblies 62 and 72 may be adjusted without losing the benefits provided by the other. More particularly, the overall rate of flow of the gas supplied to analyzer 10 through outlet line 50 may be adjusted, via valve 64, without changing either the rate of flow of gas through flow regulating assembly 72 or the setting relationship of ozone content adjusting valves 102 and 104. Conversely, the flow setting of valve 74 and/or the flow settings of ozone content adjusting valves 102 and 104 may be changed without changing the rate of flow of the gas that is supplied to analyzer 10 through outlet line 50.

This advantageous result is produced by connecting flow regulating assemblies 62 and 72 together in such a way that gas flowing at the output P of flow regulating assembly 72 is introduced into flow regulating assembly 62 at a point P2 that is upstream of valve 64. This connection assures that the gas in the third gas flow path is mixed into the gas in the first flow path prior to the arrival of the mixed gas stream at the point P1 at which the regulating action of assembly 62 is made effective. The latter condition, in turn, allows flow regulating assembly 62 to maintain an established flow rate in spite of changes in the proportions of the gases supplied thereto through the first and third gas flow paths. A similar effect will be understood to occur as gas flow is shifted between the first and second flow path by the operation of solenoid valve 60.

In view of the foregoing, it will be seen that the detector of the present invention supplies analyzer 10 with a gas stream having a flow rate which remains constant as gas flow shifts among the first, second and third flow paths, and as adjustments are made of the ozone content of the gas in the third flow path. As a result, efficiency values that are based on measurements made with the use of the detector of the invention accurately reflect the true efficiency of the NOx converter, and are free of the inaccuracies that had in the past resulted from the last mentioned shifts and adjustments. Thus, the present invention improves the accuracy of NOx conversion efficiency determinations as well as improving the stability and ease of adjustment thereof.

Figure 2:
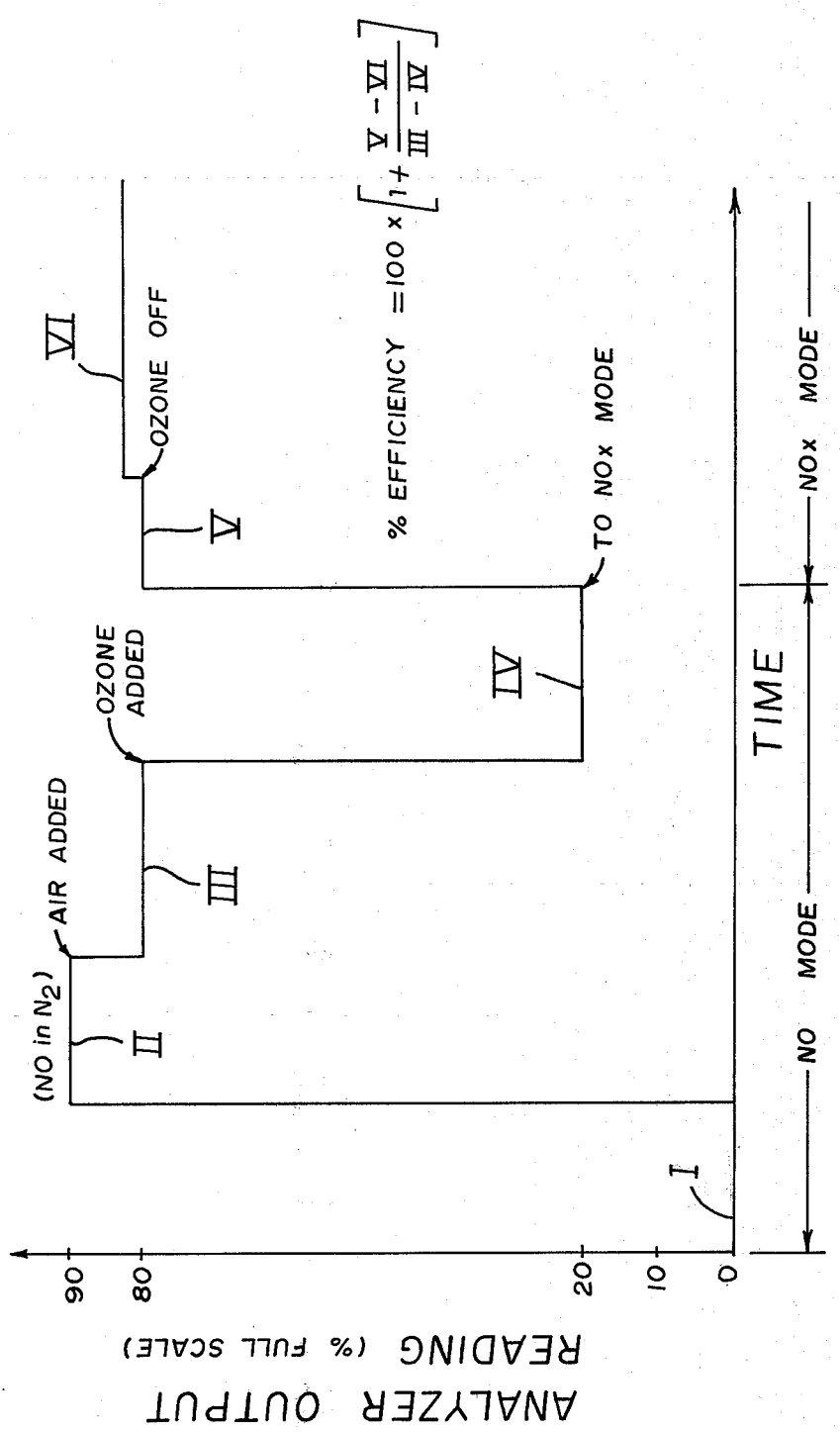
FIG. 2 is a graphic representation of the sequence of gas flow conditions that are established during the taking of series of readings for use in the conversion efficiency equation.

The gas flow conditions that occur during the course of a complete efficiency determination sequence will now be briefly described. In the first step of the sequence analyzer 10 is placed in its NO mode and switches 66, 82 and 90 are in the positions shown in FIG. 1. Under this condition, the normally closed condition of solenoid 60 causes zero gas to be supplied to analyzer 10 through the second gas flow path. This condition allows the zeroing of the output reading of analyzer 10, and is shown as plateau I of FIG. 2.

In the second step of the measurement sequence the flow of zero gas in the second flow path is cut off, and the flow of NO containing standard gas in the first flow path is established. This condition is produced as switch 66 is operated from the position shown in FIG. 1 to energize solenoid 60. Under this condition, the detector and analyzer are adjusted so that analyzer 10 correctly indicates the NO content of the gas in line 50 while reading approximately 90% of the full scale value of the analyzer range then being used. This condition is illustrated as plateau II of FIG. 2.

In the third step of the measurement sequence switch 82 is operated from the position shown in FIG. 1 to energize solenoid valve 67 and establish gas flow through the third as well as the first gas flow path. Under this condition, oxygen containing zero gas from inlet 30 is mixed with the NO containing standard gas from inlet 40, thereby diluting the latter. No ozone is introduced, however, because solenoid valves 86 and 88 are in their normally open (bypass) states. Needle valve 74 is then adjusted so that the output reading of analyzer 10 drops to 80% of its full scale value. Under this condition, flow regulating assembly 62 assures that no change occurs in the overall rate at which gas is supplied to analyzer 10. This condition is illustrated as plateau III of FIG. 2.

The fourth step of the measurement sequence occurs as switch 90 is operated from the position shown in FIG. 1 to energize coils 92 and 94 and thereby change the states of solenoid valves 86 and 88. At the same time switch 90 causes operating power to be supplied to ozone generator 100 to initiate the generation of ozone thereby. As a result of these actions, the flow of gas through the third gas flow path is shifted from the bypass path through ozone control assembly 78 to the ozonating path therethrough. This causes a portion of the oxygen in the zero gas to be converted to ozone, the proper ozone level being set in the manner previously described by adjusting needle valves 102 and 104. In accordance with EPA regulations, the ozone level is adjusted so that enough of the nitric oxide in the standard gas is oxidized to higher oxides of nitrogen that the output reading of analyzer 10 drops to 20% of its full scale value. This condition is illustrated as plateau IV of FIG. 2.

In the fifth step of the measurement sequence, analyzer 10 is switched from its NO mode to its NOx mode, thereby directing the gas entering analyzer inlet 12 through the analyzer's NOx converter. This is done in an attempt to reduce back to nitric oxide the higher oxides of nitrogen that were produced by the addition of ozone. As this occurs, the output reading of analyzer 10 moves toward its former value, i.e., plateau III of FIG. 2. As previously explained, the closeness with which the analyzer output reading approaches its former value is indicative of the extent to which the analyzer's NOx converter is completely efficient. A representative actual value is shown as plateau V of FIG. 2.

If it is known that no higher oxides of nitrogen are present in either the standard gas or the zero gas, the measurement process is for all practical purposes completed with the completion of step 5. If, however, some higher oxides are present in either gas (up to 5% is permitted under EPA regulations), an additional step is necessary to take into account the effect of those higher oxides. This step includes a return to the condition in which no ozone is introduced into the gas in the third gas path, but in which gas flow is maintained through analyzer 10. This condition is conveniently established by returning switch 90 to the position shown in FIG. 1, thereby de-energizing solenoid valves 86 and 88 and ozone generator 100. This condition is illustrated as plateau IV in FIG. 2.

In summary, the above-described sequence of steps involves the establishment of a succession of gas flow states for which the output readings of analyzer 10 are recorded. Once all of these output readings are available they are substituted into the efficiency formula shown in FIG. 2 for the final conversion efficiency calculation. Because this sequence of steps and the resulting calculation are meaningful only for the analyzer output range used during the measurement process, the entire sequence of steps must be repeated for each additional output range of analyzer 10.

In performing the above-described measurement sequence, the conversion efficiency detector of the invention greatly facilitates proceeding from one step to the next. In making the adjustments necessary to establish plateaus II and III of FIG. 2, for example, the quantity of air added may be adjusted without deviating from the flow rate that existed during the establishment of plateau I of FIG. 2. Similarly, the ozone level changes produced by adjusting valves 102 and 104 may be made without significant effect on the flow rates established by valves 64 and 74 during preceding steps. As a result, a user may proceed confidently from step to step, knowing that the conditions upon which the measurements are premised are maintained. In addition, the present invention greatly facilitates the adjustment of the ozone level by providing a wide range yet finely controllable adjustment of the quantity of ozone introduced by generator 100. Thus, the detector contemplated by the present invention improves both the accuracy and the speed with which efficiency determinations are made.

While the invention has been described with reference to a specific embodiment that reflects the best mode known to the inventors for practicing the present invention, other embodiments will be obvious to those skilled in the art. Accordingly, the true scope of the present invention should be evaluated only in reference to the following claims.

What is claimed is:

1. In a conversion efficiency detector having a first inlet for connection to a source of a nitric oxide containing standard gas, a second inlet for connection to a source of an oxygen containing zero gas, an outlet for connection to the sample inlet of an oxides of nitrogen analyzer, and an ozone generator for converting to ozone a portion of the oxygen in the zero gas, the improvement comprising:
   (a) first and second adjustable flow regulating means for regulating the flow of gases therethrough,
   (b) means for connecting the first flow regulating means between the first inlet and the outlet, and
   (c) means for connecting the second flow regulating means and the ozone generator between the second inlet and the first flow regulating means, so that the rate of flow of gas through the second flow regulating means may be adjusted without changing the rate of flow of gas through the first regulating means.

2. A detector as set forth in claim 1 in which each flow regulating means includes a flow adjusting device and a flow controller having an inlet, an outlet and a control line, the flow adjusting devices being connected between the outlets and the control lines of the respective controllers.

3. A detector as set forth in claim 2 in which the control line of the second flow regulating means is connected between the outlet of the controller and the flow adjusting device of the first flow regulating means.

4. A detector as set forth in claim 1 including a series flow control device connected in series with the ozone generator and a parallel flow control device connected in parallel with the ozone generator, the series and parallel control devices serving to jointly control the ozone content of the gas flowing out of the second flow regulating means.

5. A detector as set forth in claim 4 in which the parallel flow control device is maintained in a fixed, low flow resistance condition during adjustment of the series flow control device, and in which the series flow control device is maintained in a fixed, low flow resistance condition during adjustment of the parallel flow control device.

6. A detector as set forth in claim 4 in which the series flow control device serves as means for reducing the ozone content of the gas flowing through the second flow regulating means below the nominal value thereof, and in which the parallel flow control device serves as means for increasing the ozone content of the gas flowing through the second flow regulating means above the nominal value thereof.

7. A detector as set forth in claim 4 in which one of said flow control devices is a fixed flow resistance and in which the other of said flow control devices is a manually adjustable valve.

8. A detector as set forth in claim 1 including bypass means having a first state and a second state, said bypass means serving as means for bypassing the flow of gas around the ozone generator when in said first state, and for directing the flow of gas through the ozone generator when in said second state.

9. A detector as set forth in claim 8 in which operating power is applied to the ozone generator only when the bypass means is in its second state.

10. In a conversion efficiency detector having a first inlet for connection to a source of a nitric oxide containing standard gas, a second inlet for connection to a source of an oxygen containing zero gas, and an outlet for connection to the sample inlet of an oxides of nitrogen analyzer, the improvement comprising:
(a) a first adjustable flow regulator, connected between the first inlet and the outlet, for regulating the flow of gas to the outlet,
(b) a second adjustable flow regulator, connected between the second inlet and the first adjustable flow regulator, for regulating the flow of gas supplied thereto, and
(c) an ozone control assembly for introducing ozone into the gas flowing out of the second adjustable flow regulator, said ozone control assembly including an ozone generator and ozone control means for controlling the quantity of said ozone.

11. A detector as set forth in claim 10 in which the first adjustable flow regulator includes a flow controller having input, output and control lines and a flow rate adjustment valve, the adjustment valve being connected between the output and control lines of the flow controller; and in which the second adjustable flow regulator is connected to the first adjustable flow regulator between the output line and the adjustment valve thereof.

12. A detector as set forth in claim 10 in which the ozone control assembly includes a first bypass valve upstream of the ozone generator and a second bypass valve downstream of the ozone generator, said bypass valves together serving the controllably bypass gas flow around the ozone generator, and in which operating power is applied to the ozone generator only when the first and second bypass valves do not bypass gas flow around the ozone generator.

13. A detector as set forth in claim 10 or 11 in which said ozone control means includes a parallel flow control device connected in parallel with the ozone generator and a series flow control device connected in series with the ozone generator.

14. A detector as set forth in claim 13 in which the parallel flow control device is maintained in a fixed flow resistance condition when the condition of the series flow control device changes, and in which the series flow control device is maintained in a fixed flow resistance condition when the condition of the parallel flow control device changes.

15. A detector as set forth in claim 13 in which one of the flow control devices is a fixed flow resistance and in which the other of said flow control devices is a manually adjustable valve.

16. A detector as set forth in claim 10 including source-select valve means, connected between the detector outlet and the sample inlet, for selectably connecting the sample inlet to a source of sample gas or to the detector outlet.

17. In a conversion efficiency detector having a first inlet for connection to a source of a nitric oxide containing standard gas, a second inlet for connection to a source of an oxygen containing zero gas, and an outlet for connection to the sample inlet of an oxides of nitrogen analyzer, the improvement comprising:
an ozone control assembly having:
(a) an ozone generator for converting to ozone a portion of the oxygen in the zero gas,
(b) a first flow control device connected in series with the ozone generator, and
(c) a second flow control device connected in parallel with the ozone generator, and
means for connecting the ozone control assembly between the second inlet and the outlet to controllably introduce ozone into the gas flowing between the first inlet and the outlet, said flow control devices jointly controlling the quantity of ozone introduced by the ozone control assembly.

18. A detector as set forth in claim 17 in which the first and second flow control devices are manually adjustable valves.

19. A detector as set forth in claim 18 in which the first flow control valve is adjusted while the second flow control valve is substantially fully open, and in which the second flow control valve is adjusted while the first flow control valve is substantially fully open.

20. A detector as set forth in claim 17 in which one of the flow control devices is a fixed flow resistance and in which the other of the control devices is a manually adjustable valve.

21. A detector as set forth in claim 17, 18, 19, or 20 including a third flow control device connected in series with the ozone control assembly, the combined effective flow resistance of the first and second flow devices being relatively small in relation to the flow resistance of the third flow control device.

22. A detector as set forth in claim 17 including means for controllably bypassing gas flow around the ozone control assembly.

23. A detector as set forth in claim 22 in which operating power is removed from the ozone generator when said bypass means is bypassing gas flow around the ozone control assembly, and in which the ozone generator is supplied with a substantially constant level of operating power when said bypass means is not bypassing gas flow around the ozone control assembly.

* * * * *